United States Patent [19]

Broselow

[11] Patent Number: 4,823,469

[45] Date of Patent: * Apr. 25, 1989

[54] MEASURING TAPE FOR DIRECTLY DETERMINING PHYSICAL TREATMENT AND PHYSIOLOGICAL VALUES AND PROCEDURES

[76] Inventor: James B. Broselow, Rte. 12, Hickory, N.C. 28602

[*] Notice: The portion of the term of this patent subsequent to Dec. 22, 2004 has been disclaimed.

[21] Appl. No.: 133,956

[22] Filed: Dec. 17, 1987

Related U.S. Application Data

[63] Continuation of Ser. No. 910,490, Sep. 23, 1986, Pat. No. 4,713,888, which is a continuation-in-part of Ser. No. 789,497, Oct. 21, 1985, abandoned.

[51] Int. Cl.$^4$ .............................................. G01B 3/02
[52] U.S. Cl. ...................................... 33/760; 33/512; 33/679.1
[58] Field of Search ................ 33/137 R, 137 L, 138, 33/140, 494, 483, 511, 512, 515; 235/86, 87 A, 7 A; 728/1 R, 774; 604/189; 5/508; 283/900; 434/262

[56] References Cited

U.S. PATENT DOCUMENTS

| | | | |
|---|---|---|---|
| 3,020,643 | 2/1962 | Moran | 33/512 |
| 3,196,551 | 7/1965 | Provost et al. | 33/515 |
| 3,336,674 | 8/1967 | Higgins et al. | 33/137 R |
| 3,520,293 | 7/1970 | Atherholt | 33/515 |
| 4,366,623 | 1/1983 | Bergquist | 33/140 |
| 4,713,888 | 12/1987 | Broselow | 33/137 R |

FOREIGN PATENT DOCUMENTS

| | | | |
|---|---|---|---|
| 5060 | 8/1884 | United Kingdom | 33/137 R |
| 423343 | 2/1911 | France | 33/137 R |
| 812717 | 4/1959 | United Kingdom | 33/137 R |

OTHER PUBLICATIONS

The Merck Manual of Diagnosis and Therapy, Berkow, Ed., 1982, pp. 514–519.
Popular Science, Dec. 1972, p. 72.

Primary Examiner—William A. Cuchlinski, Jr.
Assistant Examiner—Patrick R. Scanlon
Attorney, Agent, or Firm—W. Thad Adams, III

[57] ABSTRACT

A measuring tape has indicia thereon for measuring a patient, the indicia representing increments of a physical treatment or physiological procedure based upon a correlation between the length of a patient and that procedure. Cardiopulmonary resuscitation is an example of the type of values which can be correlated to body length and placed on the tape.

7 Claims, 3 Drawing Sheets

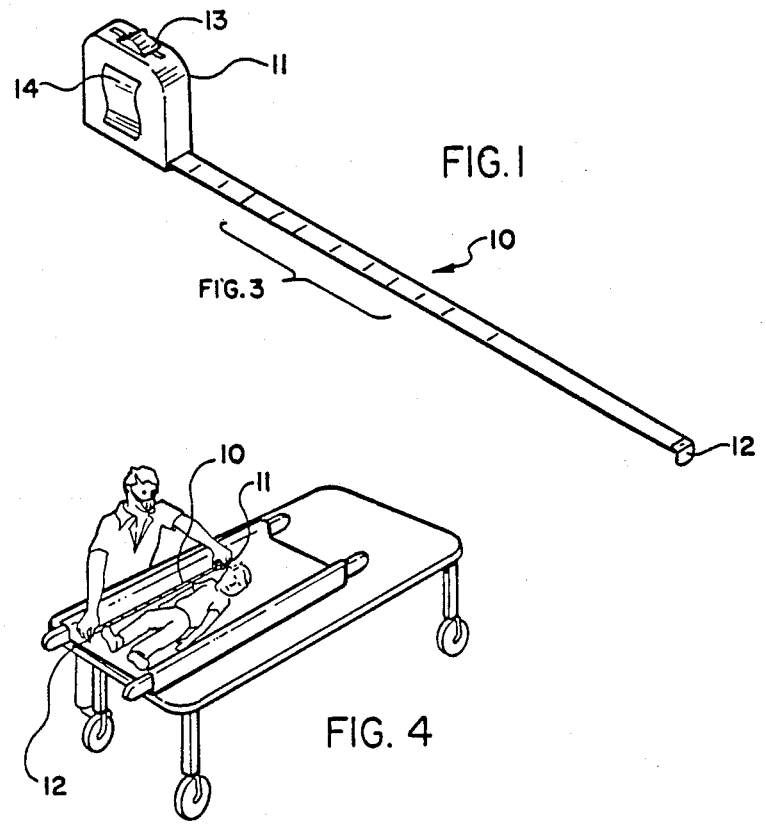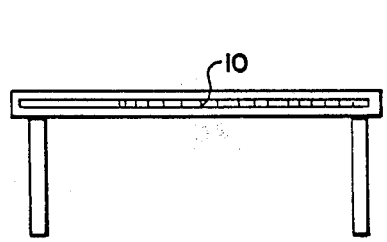

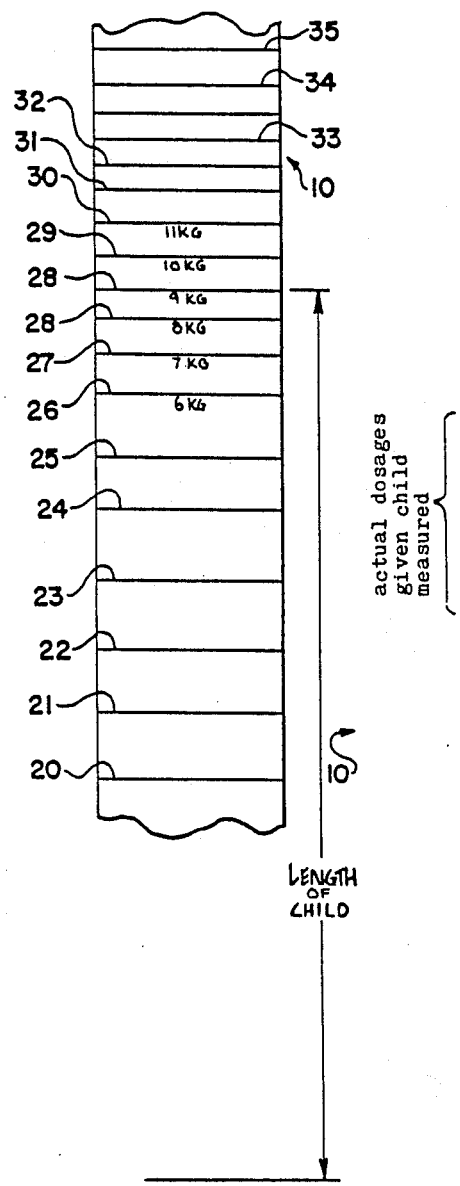

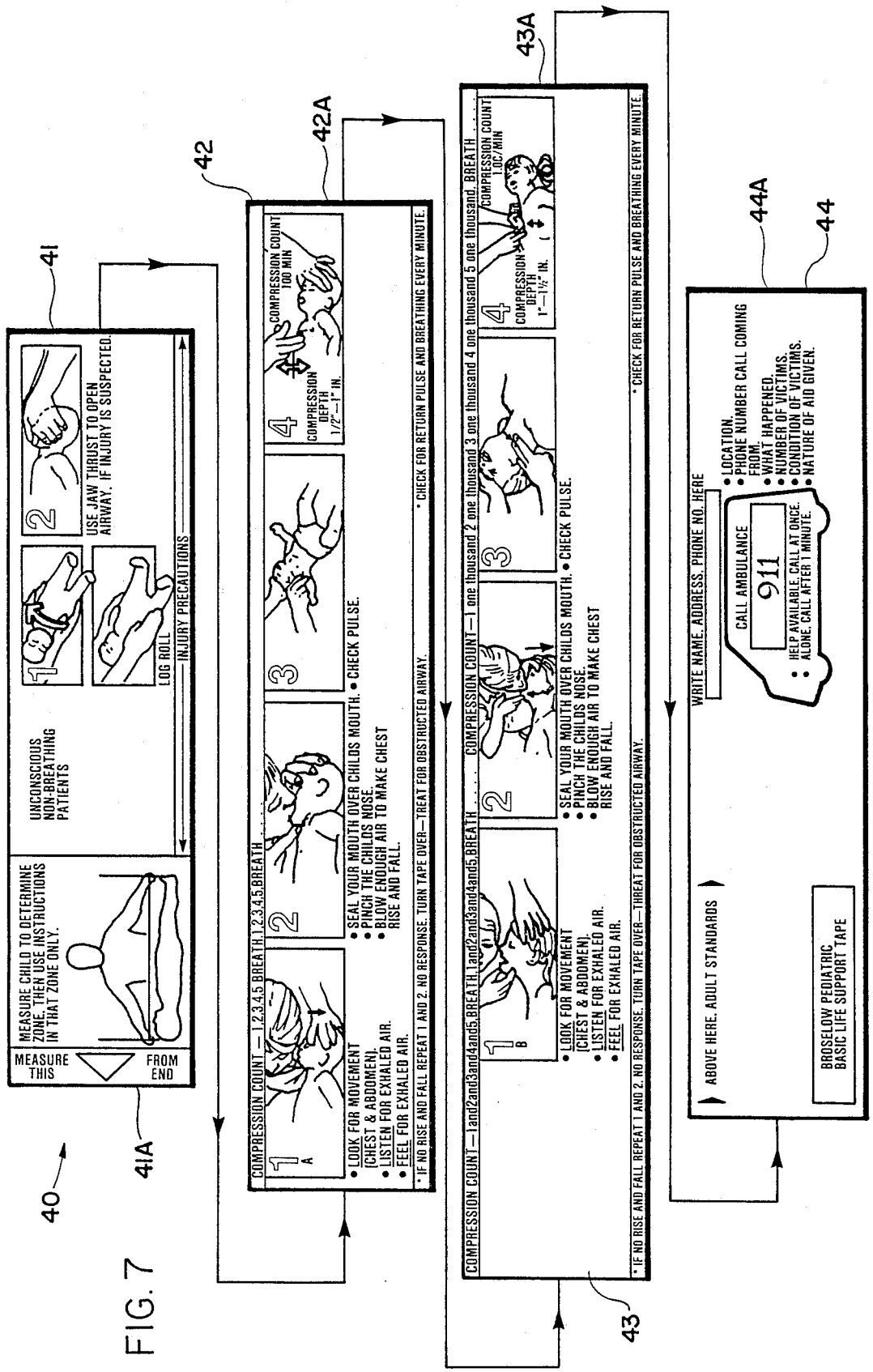

MEASURING TAPE FOR DIRECTLY DETERMINING PHYSICAL TREATMENT AND PHYSIOLOGICAL VALUES AND PROCEDURES

This application is a continuation-in-part of Applicant's earlier filed application Ser. No. 910,490, filed Sept. 23, 1986, which issued on Dec. 22, 1987 as U.S. Pat. No. 4,713,888, which application was a continuation-in-part of Ser. No. 789,497 filed Oct. 21, 1985, abandoned.

TECHNICAL FIELD AND BACKGROUND OF THE INVENTION

This invention relates to a quick yet nevertheless accurate way of determining physical treatment and physiological values. The invention is particularly useful in an emergency, intensive care, or surgical environment where accurate determination of body weight has, in the past, been important in determining proper medical treatment values, such as drug dosages, etc., yet difficult to obtain because time is of the essence and scales are either not available or impractical to use because of the patient's condition.

Furthermore, as medical treatment has become more complex, drug dosages have become more critical. Since most drug dosages have been based historically on the body weight of the patient, the physician must first estimate the weight of the patient, then either consult tables to determine the appropriate dosage, or determine the dosage by memory and then multiply dosage times estimated weight for each drug. In either case, the possibility of error is present and in fact enhanced by the pressure of time and circumstance which often attend emergency medical treatment.

However, it has been recognized that in many cases weight is an inaccurate and inappropriate basis on which to determine physical treatment values, such as drug dosages, tube lengths and sizes, medical equipment settings and so forth. Yet, weight remains the most common way of determining these values. In many cases, length is a much more appropriate way to determine many physical treatment values. For example, the length of an endotracheal tube is very closely related to the overall length of a patient, whether that patient is underweight, overweight or of an ideal weight. Likewise, it is now known that an obese patient weighing significantly more than a patient of normal weight will certainly not need a proportional increase in the dosage of most drugs and, in fact, can be dosed to toxic levels in this way. This is because many drugs distribute only in the lean body tissue. Yet, patient treatment values are still most often determined by estimating the patient's weight.

SUMMARY OF THE INVENTION

Therefore, it is an object of the invention to provide a measuring tape which permits direct and accurate determination of physical treatment and physiological values and physical treatment procedures correlated to body length.

It is another object of the invention to provide a measuring tape which includes indicia thereon which provides direct reference to drug dosages, joule settings for defibrillators, endotracheal tube sizes, physiological parameters such as ideal weights, growth and development averages and the like.

It is yet another object of the present invention to provide a measuring tape which may be attached to a stretcher or the like for determination of physical treatment and physiological values without reference to weight or length charts or correlation tables.

These and other objects and advantages of the present invention are achieved by providing a measuring tape having indicia correlating body length to physical treatment and physiological values for permitting quick determination of medical treatment values or medical treatment procedures. According to a preferred embodiment of the invention, the tape comprises a flexible strip which can be used loose or can be retractably and extensibly mounted within an enclosure. The enclosure may be stationarily mounted at a fixed position on a body supporting surface for permitting the tape to be extended for measuring the body and then retracted into the enclosure for storage, or affixed permanently in its elongated position along the length of a body supporting surface for permitting the tape to be visually referred to in relation to the body lying on the surface without manipulation.

According to various embodiments, the indicia on the tape may comprise body weight indicia; drug dosages correlated to body weight, joules for defibrillation machine settings correlated to body weight, endotracheal tube sizes correlated to body weight, or physical treatment procedures such as cardiopulmonary resuscitation procedures which are administered according to the length of the patient.

BRIEF DESCRIPTION OF THE DRAWINGS

These and other objects of the present invention will be further explained with reference to the following drawings, in which:

FIG. 1 is a perspective view of one embodiment of the measuring tape according to the present invention;

FIG. 2 is an enlarged fragmentary view of the tape shown in FIG. 1 in accordance with one embodiment of the invention;

FIG. 3 is an enlarged fragmentary view of the tape shown in FIG. 1 in accordance with another embodiment of the invention;

FIG. 4 is a perspective view illustrating the manner of usage of the embodiment shown in FIG. 1;

FIG. 5 is a side elevational view of the measuring tape according to another embodiment of the invention wherein the tape is mounted for use on the side of a stretcher;

FIG. 6 is a side elevational view of the measuring tape according to another embodiment of the invention wherein the tape is affixed to the side of a stretcher in its extended form; and FIG. 7 is a top plan view of a tape according to another embodiment of the invention.

DESCRIPTION OF THE PREFERRED EMBODIMENT

Referring now specifically to the drawings, a measuring tape according to one embodiment of the invention is shown in FIG. 1 and indicated broadly at reference numeral 10. Tape 10 can be constructed with numerous differing physical characteristics. Preferably, tape 10 comprises a steel-type tape having a cupped cross-section which provides increased rigidity to the tape yet allows flexibility when needed. According to the embodiment shown in FIG. 1, the tape is retractably mounted inside an enclosure 11. One end of the tape is connected to a spring return mechanism (not shown). Measuring tape 10 is used by withdrawing the tape from enclosure 11 by means of a ring 12. To retract the tape, a button 13 on top of enclosure 11 is pushed which causes tape 10 to retract into enclosure 11. A belt clip 14 is provided so that the enclosure 11 can be secured to the user's belt or a pocket.

Referring now to FIG. 2, a view of a portion of measuring tape 10 is shown in more detail. As can be seen, the tape 10 is provided with indicia 20–35. Each indicia represent a length of measuring tape 10 correlated to body weight in kilograms. Accordingly, by measuring the body of the patient from head to toe, the ideal or lean body weight of the patient can be determined directly.

By body weight is meant statistics from the National Center for Health Statistics which have been used to plot the statistical relationship between weight and length variables for normal children. The fiftieth percentiles for boys and girls have been averaged to make a single table of length-weight relationships. This data has been transposed onto tape 10 which, in accordance with standard medical nomenclature, is marked in one kilogram increments. This information is derived from a standard medical textbook, entitled Nelson Textbook of Pediatrics, 12th Ed. 1979, Library of Congress, Cat. Card No. 81-48409. (W. B. Saunders Company). This information is summarized in Table I, below:

| KG | CENT | INCHES |
|---|---|---|
| 4 | 54.47 | 21.44 |
| 5 | 58.24 | 22.93 |
| 6 | 62.58 | 24.64 |
| 7 | 63.14 | 24.86 |
| 8 | 67.67 | 26.64 |
| 9 | 71.93 | 28.32 |
| 10 | 75.65 | 29.78 |
| 11 | 82.80 | 32.60 |
| 12 | 85.73 | 33.75 |
| 13 | 93.00 | 36.61 |
| 14 | 96.83 | 38.12 |
| 15 | 97.14 | 38.25 |
| 16 | 101.53 | 39.97 |
| 17 | 105.36 | 41.48 |
| 18 | 109.04 | 42.93 |
| 19 | 112.30 | 44.21 |
| 20 | 115.49 | 45.47 |
| 21 | 118.43 | 46.63 |
| 22 | 120.99 | 47.64 |
| 23 | 123.78 | 48.73 |
| 24 | 125.96 | 49.59 |
| 25 | 127.99 | 50.39 |
| 26 | 129.92 | 51.15 |
| 27 | 131.77 | 51.88 |
| 28 | 133.52 | 52.57 |
| 29 | 135.14 | 53.21 |
| 30 | 136.82 | 53.87 |
| 31 | 138.70 | 54.61 |
| 32 | 140.31 | 55.24 |
| 33 | 141.69 | 55.78 |
| 34 | 143.00 | 56.30 |
| 35 | 144.29 | 56.81 |
| 36 | 145.93 | 57.45 |
| 37 | 147.71 | 58.15 |
| 38 | 149.28 | 58.77 |
| 39 | 150.67 | 59.32 |
| 40 | 152.03 | 59.86 |
| 41 | 153.32 | 60.36 |
| 42 | 154.61 | 60.87 |
| 43 | 155.66 | 61.28 |

Of course, other weight tables can be used and separate measures can be used for boys and girls. It has been found that correlating weight and length in this manner achieves a much more accurate result than merely visually estimating body weight based upon the overall size of the child—the procedure now commonly followed in emergency rooms. The weight figures used are for "lean", or ideal body weight. Therefore, the measuring tape 10 automatically takes into account that, for example, drug dosage does not increase in direct proportion to an increase in weight. This is desirable since most emergency drug dosages are based on "lean" body weight since drugs do not distribute into fatty tissue at the same rate or to the same extent as into organ and muscle tissue during the time frame of emergency treatment.

The term "physical treatment values" is used throughout and has thus far referred to drug dosages and endotracheal tube lengths. Many other values can be correlated in the same manner, such as defibrillator settings, catheters, intravenous lines and the like. The term "physiological values" has been used and can refer to, for example, ideal weight per unit of length, calorie requirements for a given length, blood pressure parameters and even information concerning when certain levels of growth and development should be attained. The tape can also be used to guide parents in taking children for medical and dental examinations, and when certain steps relating to personal and dental hygiene should be commenced. Such uses are referred to as "procedures."

Referring now to FIG. 3, a still more detailed view of tape 10 is shown, specifically indicia 26–30. Here it can be seen that several items of useful information have been actually reproduced on measuring tape 10. In addition to several commonly prescribed drugs, a defibrillator setting in joules and an endotracheal tube size has been provided for quick reference by an emergency room physician or paramedic.

In addition to or in substitution of some or all of the indicia shown in FIG. 3, information concerning anesthesia dosages, antibiotic dosages and twenty-four hour maintenance fluid requirements can be included. In fact, any information which is based on body length or ideal body weight can be placed on measuring tape 10.

In addition, measuring tape 10 can be used in a number of different ways. As is shown in FIG. 4, the tape can be used as is a conventional measuring tape. That is, the enclosure 11 is placed at one end of the patient and the measuring tape 10 is extended so that the ring 12 of measuring tape 10 is at the other end of the patient. Then, the weight or other weight-correlated information is read directly off of tape 10, as described.

As is shown in FIG. 5, enclosure 11 can be mounted at the head or foot end of a stretcher. When a patient is placed on the stretcher, a measurement can be taken by extending measuring tape 10 downwardly along the length of the stretcher to the other end of the body. Another variation of the invention is shown in FIG. 6, where a measuring tape 10' is fixed along the length of a stretcher so that a reading can be taken directly without manipulating the tape at all. It is only necessary to make sure that one end of the body is adjacent one end of the tape.

The tape 10 has been described above with reference to total heel-to-crown body length. However, the term "body length" as used herein also refers to any body part length or body subsegment length to which a desired value can be correlated.

Referring now to FIG. 7, a tape 40 is broadly indicated which is used for providing quick access to physical treatment procedures based upon a scientifically valid correlation between the length of a patient and that procedure. Specifically, the tape is segmented and marked to provide proper cardiopulmonary resuscitation for differently-sized patients. As shown, tape 40 comprises a single, continuous strip divided into four segments 41, 42, 43 and 44. Proper CPR technique depends upon the length of the child. On segment 41, basic instructions are given on how to measure the child and how to take precautions for injuries to the child. In measuring the child, the end mark 41A of segment 41 is placed adjacent the head and the tape is stretched along the child's torso. If the infant is shorter in length than the distance between the end 41A and a vertical line at 42A, then the instructions appearing in panels 1A, 2, 3 and 4 on segment 42 are used as guidance to properly carry out the CPR technique. If the child's length measurement extends beyond 42A into panel 43, then the procedures illustrated in panels 1B, 2, 3 and 4 on segment 43 are carried out. As is apparent both from the pictures and the instructions, the proper techniques for administering CPR to infants and to young children differ considerably. Any child whose length extends beyond the end 44A of segment 44 is administered CPR in the same manner as an adult.

As is also shown in reference to panel 4, other information such as emergency numbers and so forth can be provided for immediate reference by the person administering the CPR.

Tapes 10, 10' and 40 can all be used for animals as well. An analogous measurement, such as from the base of the skull to the base of the tail on, for example, a dog, would be correlated to the distances on the tape. In addition, a tape such as described above can be used to indicate directly the size and location of surgical and emergency instruments. Furthermore, the location of these instruments in, for example, a supply cart can be indexed so that coded numbers, colors or the like direct the user immediately to the location for the proper instrument.

A measuring tape is described above. Various details of the invention may be changed without departing from its scope. Furthermore, the foregoing description of the preferred embodiment of a measuring tape according to the present invention is provided for the purpose of illustration only and not for the purpose of limitation—the invention being defined by the claims.

I claim:

1. A measuring tape having increments of indicia thereon for measuring a patient, said indicia representing a medically correct physical treatment procedure based upon a scientifically valid correlation between the length of a patient and that procedure.

2. A measuring tape according to claim 1, wherein the indicia on said tape comprises medical equipment sizes.

3. A measuring tape according to claim 1, wherein the indicia on said tape comprise endotracheal tube sizes correlated to body length.

4. A measuring tape according to claim 1, wherein the tape includes instructions thereon for carrying out cardiopulmonary resuscitation and the increments of indicia indicate the correct procedures to be carried out on a patient of a given length.

5. A measuring tape according to claim 1, wherein said tape comprises a flexible strip retractable and extensibly mounted within an enclosure.

6. A measuring tape according to claim 5, wherein said enclosure is stationarily mounted at a fixed position on a body supporting surface for permitting the tape to be extended for measuring a body and then retracted into the enclosure for storage.

7. A measuring tape according to claim 1, wherein said tape is affixed permanently in its elongated position along the length of a body supporting surface for permitting the tape to be visually referred to in relation to a body lying on the surface without manipulation.

* * * * *